(12) United States Patent
Kalled et al.

(10) Patent No.: US 9,387,237 B2
(45) Date of Patent: Jul. 12, 2016

(54) METHODS OF TREATING A PATIENT HAVING AN AUTOIMMUNE DISORDER BY ADMINISTERING A SOLUBLE BCMA

(71) Applicant: Biogen Idec MA Inc., Cambridge, MA (US)

(72) Inventors: Susan Kalled, Concord, MA (US); Sambasiva Rao, Franklin, MA (US)

(73) Assignee: BIOGEN MA INC., Cambridge, MA (US)

( * ) Notice: Subject to any disclaimer, the term of this patent is extended or adjusted under 35 U.S.C. 154(b) by 0 days.

(21) Appl. No.: 14/449,564

(22) Filed: Aug. 1, 2014

(65) Prior Publication Data

US 2015/0098953 A1 Apr. 9, 2015

Related U.S. Application Data

(60) Continuation of application No. 13/302,826, filed on Nov. 22, 2011, now Pat. No. 8,828,948, which is a division of application No. 12/908,767, filed on Oct. 20, 2010, now Pat. No. 8,084,030, which is a division of application No. 10/576,527, filed as application No. PCT/US2004/034514 on Oct. 20, 2004, now Pat. No. 7,850,967.

(60) Provisional application No. 60/512,880, filed on Oct. 20, 2003.

(51) Int. Cl.
| | |
|---|---|
| A61K 38/00 | (2006.01) |
| A61K 39/00 | (2006.01) |
| A61K 38/17 | (2006.01) |
| C07K 16/22 | (2006.01) |
| C07K 16/18 | (2006.01) |

(52) U.S. Cl.
CPC ........... *A61K 39/0005* (2013.01); *A61K 38/177* (2013.01); *A61K 39/0008* (2013.01); *C07K 16/18* (2013.01); *C07K 16/22* (2013.01); *A61K 2039/505* (2013.01); *A61K 2039/545* (2013.01); *A61K 2039/55* (2013.01); *A61K 2039/6056* (2013.01)

(58) Field of Classification Search
CPC ..................... A61K 39/0008; A61K 2039/545
See application file for complete search history.

(56) References Cited

U.S. PATENT DOCUMENTS

| | | | |
|---|---|---|---|
| 5,445,940 | A | 8/1995 | Brenner et al. |
| 5,624,821 | A | 4/1997 | Winter et al. |
| 5,648,260 | A | 7/1997 | Winter et al. |
| 6,869,605 | B2 | 3/2005 | Browning et al. |
| 7,112,410 | B1 | 9/2006 | Ruben et al. |
| 7,112,421 | B2 | 9/2006 | Ambrose et al. |
| 7,276,241 | B2 | 10/2007 | Schneider et al. |
| 7,635,677 | B2 | 12/2009 | Ambrose et al. |
| 2002/0172674 | A1 | 11/2002 | Jeffrey et al. |
| 2003/0095967 | A1 | 5/2003 | MacKay et al. |

FOREIGN PATENT DOCUMENTS

| | | |
|---|---|---|
| WO | WO 99/12964 A2 | 3/1999 |
| WO | WO 01/12812 A1 | 2/2001 |
| WO | WO 01/24811 A1 | 4/2001 |
| WO | WO 02/24909 A2 | 3/2002 |
| WO | WO 03/072713 * | 9/2003 |
| WO | WO 2004/094620 A2 | 11/2004 |

OTHER PUBLICATIONS

Schiemann et al., Science, 2001, 293:2111-2114.*
Yang et al., The J. Immonology, 2005, 175:2824-2824.*
Ryan et al., Mol. Cancer Ther. 2007; 6: 3009-3018.*
Cohen, Fundamental Immunology, Paul ed, Lippincott-Raven Philadelphia, PA, 1999, chapter 33 pp. 1067-1088.
Gross et al., "TACI and BCMA Are Receptors for a TNF Homologue Implicated in B-Cell Autoimmune Disease," *Nature*, 404:995-999 (2000).
Hoshino T. et al., "SI-5—Collagen Diseases and immunological Abnormality—Immunological Abnormality Due to Viral infection," 1990, vol. 21, No. 4, p. 180-183.
Inquiry issued in Japanese Patent Application No. 2006-535436 dated Aug. 7, 2013.
International Search Report for PCT/US2004/034514, mailed Apr. 6, 2005 from the International Searching Authority of the European Patent Office.
Kalled et al., "Anti-DC40 Ligand Antibody Treatment of $SNF_1$ Mice with Established Nephritis: Preservation of Kidney Fuction," *J Immunol.* 160:2158-65 (1996).
Kalled, S.L. et al., "BAFF B cell survival factor and emerging therapeutic target for autoimmune disorders." *Expert Opin. Ther. Targets* 7(1):115-123 (2003).
Kang et al., "Very Low-Dose Tolerance with Nucleosomal Peptides Controls Lupus and Induces Potent Regulatory T Cell Subsets," *J. Immunol.* 174:3247-55 (2005).
Kayagaki et al., "BAFF/BLyS Receptor 3 Binds the B Cell Survival Factor BFF Ligand through a Discrete Surface Loop and Promotes of $NF-_\kappa B2$," *Immunity*, 10:515-524 (2002).
Notice of Final Rejection issued in Japanese Patent Application No. 2006-535436 dated Oct. 26, 2011.
Notice of Reasons for Rejection issued in Japanese Patent Application No. 2006-535436 dated Nov. 22, 2010.
Pelletier et al., "Comparison of Soluble Decoy IgG Fusion Proteins of BAFF-R and BCMA as Antagonists for BAFF," *J. Bio. Chem.*, 278:33127-33133 (2003).
Schneider et al., "BAFF, a Novel Ligand of the Tumor Necrosis Factor Family, Stimulates B Cell Growth," *J. Exp. Med.*, 189:1747-1756 (1999).

(Continued)

*Primary Examiner* — Gyan Chandra
(74) *Attorney, Agent, or Firm* — Finnegan, Henderson, Farabow, Garrett & Dunner, LLP

(57) ABSTRACT

Therapeutic regimens for administration of BAFF antagonists for treatment of immunologic and related disorders are described. Regimens involve a short-term BAFF antagonist administration course followed by an extended no-treatment period prior the round of administration.

21 Claims, 2 Drawing Sheets

(56) References Cited

OTHER PUBLICATIONS

Schwartz et al., Fundamental Immunology, Paul ed., Raven Press, NY.NY., 1989, p. 837.
Sevach, Fundamental Immunology, Paul ed, Lippincott-Raven Philadelphia, PA, 1999, chapter 34 pp. 1089-1103, 1105-1125.
Stohl, W., "A Therapeutic Role for BLyS Antagonists," *Lupus*, 13:317-332 (2004).
Thompson, Jeffrey S. et al., "BAFF-R, a Newly identified TNF Receptor That Specifically Interacts with BAFF," *Science*, Sep. 14, 2001, vol. 293, pp. 2108-2111, www.sciencemag.org.
Weber, F. "Experimental Allergic Encephalomyelitis—Prophylactic and Therapeutic Treatment with the Cyclooxygenase Inhibitor Piroxicam (Feldene)," *Int Arch Allergy Appl Immunol* 95:136-141 (1991).
Angal, S. et al. (1993) "A single amino acid substitution abolishes the heterogeneity of chimeric mouse/human (IgG4) antibody" *Mol. Immunol.*, 30:105-108.
Berardi, A.C. et al. (1997) "Individual CD34+ CD38$^{low}$ CD19' CD10' Progenitor Cells From Human Cord Blood Generate B Lymphocytes and Granulocytes" *Blood*, 89:3554-3564.
Gavalchin, J. and Datta, S. K. (1987) "The NZB X SWR model of lupus nephritis. II. Autoantibodies deposited in renal lesions show a distinctive and restricted idiotypic diversity" *J Immunol.*,138(1):138-148.
Gavin, A.L. et al. (2003) "ΔBAFF, an Alternate Splice Isoform That Regulates Receptor Binding and Biopresentation of the B Cell Survival Cytokine, BAFF" *J. Biol. Chem.*, 278(40):38220-38228.
GenBank Accession No. AAD25356, "B-cell activating factor [*Homo sapiens*]" PRI Aug. 3, 1999.
GenBank Accession No. AAP57629, "Transmembrane activator and CAML interactor [*Homo sapiens*]" PRI Jun. 15, 2003.
GenBank Accession No. AF373846. "*Homo sapiens* BAFF receptor mRNA, complete cds" PRI Nov. 28, 2008.
GenBank Accession No. AF373847, "Mus Musculus BAFF receptor mRNA, complete cds" ROD Nov. 28, 2008.
GenPept UniProtKB Accession No. Q96RJ3, "Tumor necrosis factor receptor superfamily member 13C" PRI Jan. 20, 2016.
GenPept UniProtKB Accession No. S43486, "B-cell maturation factor—human" PRI Jul. 21, 2000. Replaced by UniProtKB Accession No. Q02223.
GenPept UniProtKB Accession No. Q02223, "Tumor necrosis factor receptor superfamily member 17" PRI Jan. 20, 2016.
Gross, J.A. et al. (2001) "TACI-Ig Neutralizes Molecules Critical for B Cell Development and Autoimmune Disease: Impaired B Cell Maturation in Mice Lacking BlyS" *Immunity*, 15:289-302.
Hahne, M. et al. (1998). "APRIL, a New Ligand of the Tumor Necrosis Factor Family, Stimulates Tumor Cell Growth" *J. Exp. Med.*, 188:1185-1190.
Hiramatsu, H. et al. (2003) "Complete reconstitution of human lymphocytes from cord blood CD34+ cells using the NOD/SCID/yc$^{null}$ mice model" *Blood*, 102:873-880.
Khare et al. (2000) "Severe B cell hyperplasia and autoimmune disease in TALL-1 transgenic mice" *Proc. Natl. Acad. Sci.*, 97:3370-3375.

Lund et al. (1991) "Human FcγRI and FcγRII Interact with Distinct But Overlapping Sites on Human IgG" *J. Immmunol.*, 147:2657-2662.
MacKay, F. and J.L. Browning (2002) "BAFF: A fundamental survival factor for B cells" *Nature Reviews: Immunology*, 2:465-475.
MacKay, F. et al (1999) "Mice Transgenic for BAFF Develop Lymphocytic Disorders Along with Autoimmune Manifestations" *J. Exp. Med.*, 190:1697-1710.
Marsters, S.A. et al. (2000) "Interaction of the TNF homologues BLyS and APRIL with the TNF receptor homologues BCMA and TACI" *Curr. Biol.*, 10:785-788.
Moisini, I. and Davidson, A. (2009) "BAFF: a local and systemic target in autoimmune diseases" *Clin Exp Immunol.*, 158(2):155-163.
Moore, P.A. et al. (1999) "BLyS: Member of the Tumor Necrosis Factor Family and B Lymphocyte Stimulator" *Science*. 285:260-263.
Morgan, A. et al. (1995) "The N-terminal end of the $C_H2$ domain of chimeric human IgG1 anti-HLA-DR is necessary for C1q, FcγRI and FcγRIII binding" *Immunology*, 86:319-324.
Mukhopadhyay, A. et al. (1999) "Identification and Characterization of a Novel Cytokine, THANK, a TNF Homologue That Activates Apoptosis, Nuclear Factor-κB, and c-Jun $NH_2$-Terminal Kinase" *J. Biol. Chem.*, 274:15978-15981.
Porpiglia, A.S. et al. (2003) "Reconstitution of B cell function in murine models of immunodeficiency" *Clin. Immunol.*, 107:90-97.
Rennert, P. et al. (2000) "A Soluble Form of B Cell Maturation Antigen, a Receptor for the Tumor Necrosis Factor Family Member APRIL, Inhibits Tumor Cell Growth" *J. Exp. Med.*, 192:1677-1684.
Schiemanm, B. et al. (2001) "An essential role for BAFF in the normal development of B cells through a BCMA-independent pathway" *Science*, 293(5537):2111-2114.
Shu, H-B. et al. (1999) "TALL-1 is a novel member of the TNF family that is down-regulated by mitogens" *J. Leukoc. Biol.*, 65:680-683.
Stein, J.V. et al. (2002) "APRIL modulates B and T cell immunity" *J. Clin. Invest.*, 109(12):1587-1598.
Vaux, D. (2003) "The Buzz about BAFF" *J. Clin. Invest.*, 109:17-18
Wang, H. et al. (Jul. 2001) "TACI-ligand interactions are required for T cell activation and collagen-induced arthritis in mice" *Nat. Immunol.*, 2(7):632-637.
Wu, Y. et at (2000) "Tumor Necrosis Factor (TNF) Receptor Superfamily Member TACI is a High Affinity Receptor for TNF Family Members APRIL and BLyS"*J. Biol. Chem.*, 275:35478-35485.
Xia, X-Z. et al. (2000) "TACI Is a TRAF-interacting Receptor for TALL-1, a Tumor Necrosis Factor Family Member involved in B Cell Regulation" *J. Exp. Med.*, 192:137-143.
Yan et al. "Identification of a novel receptor for B lymphocyte stimulator that is mutated in a mouse strain with severe B cell deficiency," *Curr. Biol.*, 11:1547-1552 (2001).
Yan, M. et al. (2000) "Identification of a receptor for BLyS demonstrates a crucial role in humoral immunity" *Nat. Immunol.*, 1:37-41.
Yu, G. et al. (2000) "APRIL and TALL-1 and receptors BCMA and TACI: system for regulatiing humoral immunity" *Nat. Immunol.*, 1:252-256.

* cited by examiner

METHODS OF TREATING A PATIENT HAVING AN AUTOIMMUNE DISORDER BY ADMINISTERING A SOLUBLE BCMA

This application is a continuation of U.S. patent application Ser. No. 13/302,826, filed Nov. 22, 2011, which is a divisional application of U.S. patent application Ser. No. 12/908,767, filed Oct. 20, 2010, now U.S. Pat. No. 8,084,030, issued Dec. 27, 2011, which is a divisional application of U.S. patent application Ser. No. 10/576,527, filed May 1, 2007, now U.S. Pat. No. 7,850,967, issued Dec. 14, 2010, which is a U.S. national stage entry under 35 U.S.C. 371 of International Application No. PCT/US04/34514, filed Oct. 20, 2004, which claims priority to U.S. Provisional Application No. 60/512,880, filed Oct. 20, 2003, each of which is hereby incorporated by reference in its entirety.

FIELD OF THE INVENTION

The present invention generally relates to therapeutic regimens used in treating immunologic and related disorders. More specifically, the invention relates to methods of treating autoimmune disorders utilizing antagonists of BAFF (B cell activating factor belonging to the TNF family).

BACKGROUND OF THE INVENTION

B cells play a central role in acquired immunity. These cells possess the unique ability to mount a rapid and directed antibody (Ab) response against foreign antigens (Ag), and to act as Ag presenting cells. To maintain B cell homeostasis and a self-tolerant state, it is necessary to generate a continuous pool of B cell precursors that will mature and migrate to peripheral organs, as well as maintain a process of negative selection to eliminate autoreactive B cells. Dysregulation in the B cell developmental process could lead to a block in B cell development, and thus immune deficiency, or conversely, to en escape and expansion of self-reactive B cells leading to autoimmunity.

Generation of high affinity, somatically hypermutated autoantibodies is one of the hallmarks of autoimmune conditions. The autoantibodies can cause severe tissue damage (e.g., as in lupus nephritis) or loss of blood components (e.g., as in immune thrombocytopenia purpura). The prevailing treatment strategies for autoimmune disorders employ global immunosuppressants that have harmful side effects with long-term use.

Recent discovery of the B cell survival and maturation factor BAFF (also known as TALL-1, THANK, BLyS, zTNF4, and TNFSF13B) provided a unique opportunity for developing targeted intervention strategies for autoreactive B cell function. Elucidation of the role of BAFF in acquired immunity has been rapid since its first description as a B cell growth factor. BAFF (Accession No. AAD25356) is described in, e.g., Schneider et al (1999) J. Exp. Med., 189: 1697-1710; PCT Publication WO 99/12964 and U.S. patent application Ser. No. 09/911,777. Studies have indicated that higher than normal levels of BAFF may contribute to the pathogenesis of autoimmune diseases, such as systemic lupus erythematosus (SLE) and rheumatoid arthritis. For a review, see, e.g., Mackay et al. (2002) Nature Reviews: Immunology, 2:465-475; Kalled et al. (2003) Expert Opin. Ther. Targets, 7(1):115-23.

BAFF has been implicated in Costimulation of B cells (Moore at al. (1999) Science, 285:260-263; Schneider et al. (1999) J. Exp. Med., 189:1747-1756; Mukhopadhyay et al. (1999) J. Biol. Chem., 274:15978-15981); increased B cell proliferation (Moore et al. (1999) Science, 285:260-263); and increased survival of normally deleted B cells (Khare et al. (2000) Proc. Natl. Acad. Sci., 97:3370-3375; Gross et al. (2000) Nature, 404:995-999; Mackay et al. (1999) J. Exp. Med., 190:1697-1710). Three cognate receptors for BAFF have been identified: (1) B cell maturation antigen (BCMA; Accession No. S43486; Gross et al. (2000) Nature, 404:995-999; PCT Publication WO 01/12812; U.S. patent application Ser. No. 10/077,137); transmembrane activator and cyclophilin ligand interactor (TACI; Accession No. AAP57629; Gross et al., supra); and most recently, BAFFR (also called BR3; Accession No. AF373846; Thompson et al. (2001) Science, 293:2108-2111). BAFFR is the only one of the three receptors that is specific for BAFF (Thompson et al., supra). BCMA and TACI bind not only to BAFF but also to another TNF family ligand, APRIL (Yu et al. (2000) Nat. Immunol., 1:252-256; Wu et al. (2000) J. Biol. Chem., 275:35478-35485; Rennert et al. (2000) J. Exp. Med., 192:1677-1684; PCT Publication WO 0124811; U.S. patent application Ser. No. 10/115,192).

While BAFF has been unambiguously identified as a factor required for B cell survival and maturation, the role of APRIL in B cell homeostasis remains less well understood. APRIL was originally found to stimulate growth of tumor cells in vitro and in vivo (Hahne et al. (1998) J. Exp. Med., 188:1185-1190). Recent reports demonstrated that APRIL may act also as a costimulator of primary B and T cells in vitro and stimulate IgM production by peripheral blood B cells in vitro (Yu et al. (2000) Nat. Immunol 1:252-256; Marsters et al. (2000) Curr. Biol., 10:785-788). In vivo administration of APRIL, like BAFF, results in splenomegaly due to expansion of the B cell population and an increase in the percentage of activated T cells (Yu et al. (2000) Nat. Immunol., 1:252-256), suggesting that APRIL may be involved in lymphoid homeostasis. Based on data generated using APRIL-transgenic mice, APRIL appears to play a role in T cell-independent type 2 (TI-2) humoral responses (Stein et al. (2002) J. Clin. Invest., 109(12): 1587-1598). Further, data generated using A/WySnJ mice demonstrate that APRIL is not required for B cell development and function (Thompson et al., supra).

Soluble forms of BAFF receptors have been made by fusing their extracellular domains to the Fc portion of immunoglobulin. Treatment of normal mice with such a soluble form of TACI or BCMA (TACI-Fc or BCMA-Fc) leads to reduced B cell numbers and a lack of humoral response (Shu et al. (1999) J. Leukoc. Biol., 65:680-683; Yan et al. (2000) Nat. Immunol., 1:37-41; Xia et al. (2000) J. Exp. Med., 192:137-143; Wang et al. (2001) Nat. Immunol., 2:632-637; Yu et al. (2000) Nat. Immunol., 1:252-256). For example, in a mouse modal for rheumatoid arthritis, an autoimmune disease that involves both B and T cell components, TACI-Fc substantially inhibits inflammation and slows disease progression (Wang et al. (2001) Nat. Immunol., 2(7):632-637). These effects are thought to be attributed to BAFF sequestration because BAFF-deficient mice have a phenotype similar to that of TACI-Fc- or BCMA-Fc-treated mice (almost complete loss of mature B cells and a severely compromised humoral response) (Schiemann et al. (2001) Science, 293:2111-2114; Gross et al. (2001) Immunity, 15:289-302) Although a five-week treatment of NZBWF1 with TACI-Ig lead to a reduction in SLE symptoms at 12 weeks after the treatment, no reduction in autoantibodies was observed, indicating that a longer course of treatment may be necessary (Gross et al. (2000) Nature, 404(6781):995-999).

Recently, BAFF-specific agents, including BAFFR-Fc and BAFF antibodies, have been developed for treatment of autoimmune and other disorders (see, e.g., U.S. patent application Ser. Nos. 09/911,777; 10/380,703; 10/045,574; and 60/458,707); Kalled et al. (2003) Expert Opin. Ther. Targets, 7(1):115-23). Once the administration of a BAFF-specific agent has ceased and the agent is eliminated from the bloodstream, B cell reconstitution to pre-treatment levels, including recovery of pathogenic B cells, is expected to occur within about 8 weeks (see, e.g., Porpiglia et al. (2003) Clin. Immunol., 107:90-97; Berardi et al. (1997) Blood, 89:3554-3564; Hiramatsu et al. (2003) Blood, 102:873-880). As a result, frequent administration of these drugs, at intervals of less than 8 weeks, may be necessary to maintain therapeutic benefits.

Therefore, new therapeutic strategies are still needed for the treatment of immune and related disorders.

SUMMARY OF THE INVENTION

The present invention results from the realization that effective treatment of immunologic disorders can be accomplished by a short-term administration of a therapeutically effective amount of a BAFF antagonist, thereafter, temporarily discontinuing the administration of the antagonist for an extended period prior to the next round of the administration.

The invention is based, in part, on the surprising finding that a short-term 4-week administration of BAFFR-Fc to nephritic SNF1 mice with mild-to-moderate SLE results in a long-term clinical benefit (at least 6 months). Although B cell recovery does take place following administration of BAFFR-Fc, the newly emerging B cells are substantially non-pathogenic. The invention is further based, on the discovery and demonstration that the clinical effect of the short-term BAFFR-Fc administration in the SNF1 mice is significantly more pronounced and long-lasting as compared to the clinical effect observed upon administration of TACI-Fc in the same model.

The present invention provides methods for treating immunologic and related disorders in mammals, in particular autoimmune disorders, and includes (but is not limited to) methods for inhibiting autoantibody production, and/or inhibiting the generation of pathogenic B cell population in a mammal. The invention further provides methods for treating renal fibrosis and/or improving renal function, such as, e.g., pressure filtration, selective reabsorption, tubular secretion, and systemic blood pressure regulation. The invention yet further provides methods for decreasing cardiac inflammation. Methods of administration and compositions used in the methods of the inventions are also provided.

In certain embodiments, the method of treating a patient having an immunologic disorder, comprises:
(a) administering to the patient a therapeutically effective amount of a BAFF (B cell activating factor belonging to the TNF family) antagonist at least once or at one or more intervals of less than N weeks;
(b) temporarily discontinuing the administration of step (a) for N weeks or longer; and
(c) repeating steps (a) and (b) at least once;
wherein N is 8, 9, 10, 11, or 12.

In some embodiments, the BAFF antagonist is a soluble BAFF receptor (e.g., BAFFR, BCMA, or TACI), an anti-BAFF antibody, or an anti-BAFF receptor antibody. In certain embodiments, the BAFF antagonist is BAFF-specific such as, for example, soluble BAFFR.

Additional aspects of the invention will be set forth in part in the following description, and in part will be understood from the description or may be learned by practice of the invention.

BRIEF DESCRIPTION OF THE SEQUENCES

SEQ ID NO:1 is an amino acid sequence of human BAFFR (GenBank™ Accession No, AF373846). Special features noted in the Sequence Listing for this sequence: residue 1—none or any amino acid; residue 2—methionine, none, or any amino acid; residue 21—valine (wild type), asparagine, or another amino acid; residue 28—lysine (wild type), proline, or another amino acid; residue 47—none, any amino acid, or alanine.

SEQ ID NO:3 is an amino acid sequence of human BAFFR-Fc fusion protein, which includes a signal sequence (amino acids 1-22) and a human IgG1 Fc portion (amino acids 95-321). Special features noted in the Sequence Listing for this sequence: residue 41—valine (wild type), asparagine, or another amino acid; residue 48—lysine (wild type), proline, or another amino acid; residue 67—none, any amino acid, or alanine.

SEQ ID NO:2 is an amino acid sequence of murine BAFFR (GenBank™ Accession No. Q96RJ3).

SEQ ID NO:4 is an amino acid sequence of murine BAFFR-Fc fusion protein, which includes a signal sequence (amino acids 1-22) and a murine IgG1 Fc portion (amino acids 88-316).

SEQ ID NO:5 is an amino acid sequence of a BAFF-binding peptide derived from BAFFR.

SEQ ID NO:6 is an amino acid sequence of a minimal deletion in ΔBAFFR described in U.S. Patent Application No. 60/458,707.

BRIEF DESCRIPTION OF THE FIGURES

FIGS. 1A and 1B show representative kidney sections from untreated mice of 9 and 50 weeks of age, respectively. Two groups of mice were administered either 200 µg of murine BAFFR-Fc or 200 µg of mIgG1, two times per week for four consecutive weeks starting at 23 weeks of age, and sacrificed at the age of 50 or 51 weeks, respectively. FIGS. 1C and 1D show representative kidney sections from BAFFR-Fc- and mIgG1-treated mice, respectively.

FIGS. 2A and 2B show representative MLN sections from untreated mice of 9 and 50 weeks of age, respectively. Two groups of mice were administered either 200 µg of murine BAFFR-Fc or 200 µg of mIgG1, two times per week for four consecutive weeks starting at 23 weeks of age, and sacrificed at the age of 50 or 51 weeks, respectively. FIGS. 2C and 2D show representative MLN sections from BAFFR-Fc- and mIgG1-treated mice, respectively.

DETAILED DESCRIPTION OF THE INVENTION

Figure 1A:
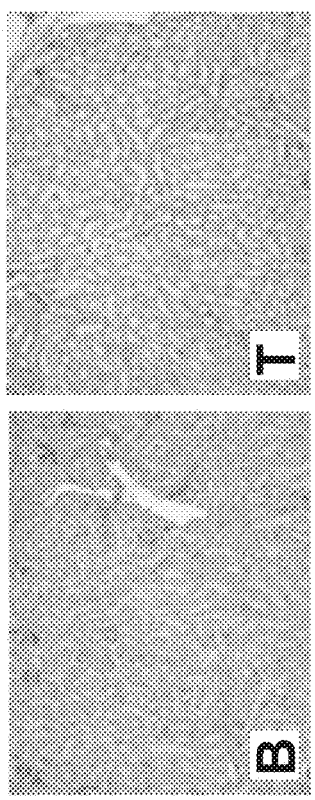
FIGS. 1A-1D demonstrate that a short-term BAFFR-Fc treatment inhibits renal lymphocyte infiltration in the kidneys of SNF1 mice as assessed by immunohistochemistry on paraffin-embedded kidney sections using biotin-anti-B220 mAb for B cells and anti-CD3 for T cells (50× magnification).
Figure 1B:
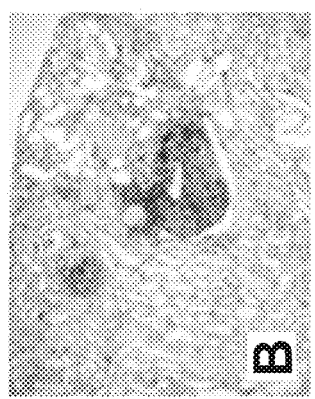
Figure 1C:
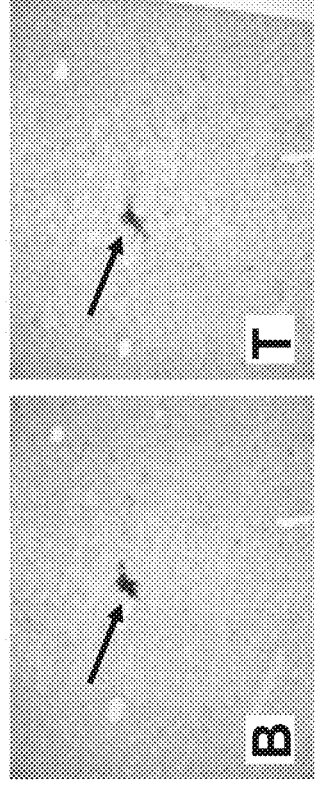
Figure 1D:
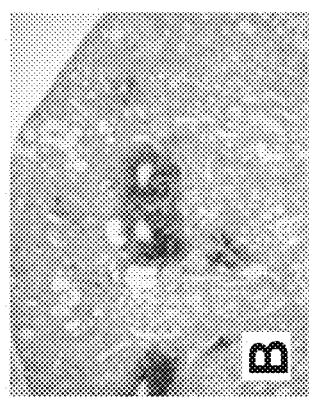

In order that the present invention may be more readily understood, certain terms are first defined. Additional definitions are set forth throughout the detailed description.

The term "antibody," as used herein, refers to an immunoglobulin or a part thereof, and encompasses any polypeptide comprising an antigen-binding site regardless of the source, method of production, and other characteristics. The term includes but is not limited to polyclonal, monoclonal, monospecific, polyspecific, non-specific, humanized, single-chain, chimeric, synthetic, recombinant, hybrid, mutated, and CDR-grafted antibodies. The term "antigen-binding domain" refers to the part of an antibody molecule that comprises the area specifically binding to or complementary to a part or all of an antigen. Where an antigen is large, an antibody may only bind to a particular part of the antigen. The "epitope," or "antigenic determinant" is a portion of an antigen molecule that is responsible for specific interactions with the antigen-binding domain of an antibody. An antigen-binding domain may be provided by one or more antibody variable domains (e.g., a so-called Fd antibody fragment consisting of a $V_H$ domain). An antigen-binding domain comprises an antibody light chain variable region ($V_L$) and an antibody heavy chain variable region ($V_H$). The terms "anti-BAFF antibody" and "antibody directed against BAFF" refer to any antibody that specifically binds to at least one epitope of BAFF.

The term "BAFF" refers to B cell-activating factor, characterized by expression in immune cells and its role as a B cell survival factor. A summary of BAFF's characteristics is provided in Mackay et al. (2002) Nature Reviews: Immunology 2:465-475 and in Gavin et al. (2003) J. Biol. Chem., 278(40): 38220-8.

As used herein, "BAFF antagonist" generally refers to any compound that directly downregulates the biological activity of BAFF. A molecule "directly downregulates" the biological activity of BAFF by interacting with a BAFF, BAFF gene, a BAFF transcript, or a BAFF receptor. A BAFF antagonist may, for example, bind to and neutralize the activity of BAFF; decrease BAFF expression levels; affect stability of BAFF; affect proteolytic cleavage of the membrane-bound form of BAFF into the soluble form; interfere with the binding of BAFF to one or more receptors; or it may interfere with intracellular signaling of a BAFF receptor. BAFF antagonists may be proteinaceous (e.g., antibodies, receptor fusion proteins, peptides) or non-proteinaceous molecules (e.g., small organic molecules (≤500 Da)). Methods for assessing neutralizing biological activity of BAFF antagonists are known in the art.

The term "BAFFR," unless otherwise stated, refers to a protein that comprises at least a portion of wild-type or mutant receptor for BAFF, other than BCMA or TACI, that is capable of binding to BAFF. It has been determined that the BAFF-binding domain of human BAFFR contains amino acids 27 to 32 of SEQ ID NO:1. BAFFR is further defined in PCT Publication WO 0224909 and U.S. patent application Ser. Nos. 10/380,703 and 60/458,707, and specifically includes, but is not limited to, human BAFFR (SEQ ID NO:1; Accession No. AAD25356; amino acid 47 of SEQ ID NO:1 is not present in some isoforms) and murine BAFFR (SEQ ID NO:3; Accession No. Q96RJ3). BAFFR also refers to naturally occurring variants, e.g., the splice variant containing an alanine at amino acid 47 of SEQ ID NO:1 corresponding to amino acid 67 of SEQ ID NO:2, as well as functional mutated forms of BAFFR, e.g., human BAFFR having mutations at least at amino acids 21 and 28 of SEQ ID NO:1 (e.g., V21N and L28P). The terms "BAFFR-Fc" and "BAFFR-Ig" refer to a fusion protein comprising BAFFR and antibody constant region sequences, such as, for example, an Fc portion.

The term "BAFF-specific antagonist" refers to a compound that: (1) has the ability to counteract the effect(s) of BAFF in vivo or in vitro, e.g., by competitive blockage of one or more BAFF receptors, and (2) under physiologic conditions preferentially forms a relatively stable complex with BAFF but not with other ligands of the TNF family, such as, e.g., APRIL. Typically, the binding is considered specific when the affinity constant Ka for BAFF is higher than 106 M-1, preferably higher than 108 M-1, while the affinity for another TNF family ligand is lower than 106 M-1, preferably lower than 105 M-1. A skilled artisan recognizes that under certain conditions a low affinity but high avidity binding may also be specific even though Ka of the interaction may be relatively low. In some embodiments, affinity constant Ka of a BAFF-specific antagonist for at least one isoform of BAFF is preferably greater than 106 M-1, 107M-1, 108 M-1, 109 M-1, 1010 M-1, 1011 M-1, or 1012 M-1.

The phrase "substantially identical" means that a relevant amino acid sequence is at least 70%, 75%, 80%, 85%, 90%, 95%, 97%, 98%, 99%, or 100% identical to a given sequence. By way of example, such sequences may be variants derived from various species, or they may be derived from the given sequence by truncation, deletion, amino acid substitution or addition. Percent identity between two amino acid sequences may be determined by standard alignment algorithms such as, for example, Basic Local Alignment Tool (BLAST) described in Altschul et al. (1990) J. Mol. Biol., 215:403-410, the algorithm of Needleman et al. (1970) J. Mol. 48:444-453, or the algorithm of Meyers et al. (1988) Comput. Appl. Biosci., 4:11-17. Such algorithms are incorporated into the BLASTN, BLASTP, and "BLAST 2 Sequences" programs (see www.ncbi.nlm.nlh.gov/BLAST). When utilizing such programs, the default parameters can be used. For example, for nucleotide sequences the following settings can be used for "BLAST 2 Sequences": program BLASTN, reward for match 2, penalty for mismatch −2, open gap and extension gap penalties 5 and 2 respectively, gap x_dropoff 50, expect 10, word size 11, filter ON. For amino acid sequences the following settings can be used for "BLAST 2 Sequences": program BLASTP, matrix BLOSUM62, open gap and extension gap penalties 11 and 1 respectively, gap x_dropoff 50, expect 10, word size 3, filter ON.

The term "immunologic disorder" refers to disorders and conditions in which an immune response is aberrant. The aberrant response can be due to (a) abnormal proliferation, maturation, survival, differentiation, or function of immune cells such as, for example, T or B cells. Example of immunologic disorders include, but are not limited to, rheumatoid arthritis (RA), asthma, psoriasis, multiple sclerosis (MS), inflammatory bowel disease (IBD), Crohn's disease, systemic lupus erythematosis (SLE), type I diabetes, Wegener's granulomatosis, transplant rejection, graft-versus-host disease (GVHD), hyperproliferative immune disorders, autoimmune diseases, B cell cancers, immunomodulation, antibody-mediated pathologies (e.g., ITCP, myasthenia gravis, and the like), and Sjogren's syndrome. The disorders that can be treated using the compositions and methods of the present invention include but are not limited to disorders described in PCT Publication WO 02/24909 and U.S. patent application Ser. Nos. 09/911,777; 10/380,703; 10/045,574; and 60/458, 707.

The term "therapeutic" and cognates thereof, as used herein, refer to amelioration of clinical manifestations of a disorder, or production of a desired biological outcome. Examples of desirable outcomes include: reduced B cell hyperplasia; reduced autoantibody titer; reduced pathogenic B cell population; reduced cardiac inflammation; improving renal function (e.g., pressure filtration, selective reabsorption, tubular secretion, and systemic blood pressure regulation), slowed progression renal fibrosis, reduced renal lymphocyte infiltration; reduced lymphadenopathy, etc. Outcomes can be determined using methods known in the art and/or as described herein.

The term "pathogenic B cell" refers to a B cell that produces autoantibody which contributes to disease pathology.

The invention is based, in part, on the surprising finding that a short-term 4-week administration of BAFFR-Fc to nephritic SNF1 mice with mild-to-moderate systemic lupus erythematosus (SLE) results in a long-term clinical benefit (at least 6 months). Given a short circulatory half-life of BAFFR-Fc in SNF1 mice (3.7 days), once BAFFR-Fc administration has ceased and BAFFR-Fc is eliminated from the bloodstream, B cell reconstitution is expected to occur within about 8 weeks. In experiments leading to the present invention, B cell recovery did take place following administration of BAFFR-Fc. However, the newly emerging B cells were found to be substantially non-pathogenic. The invention is further based, on the discovery and demonstration that the conical effect of the short-term BAFFR-Fc administration in the SNF1 mice is significantly more pronounced and long-lasting as compared to TACI-Fc in the same model.

Methods of the inventions, compositions used therein, and other aspects of the invention are described in detail below.

Methods

The invention provides therapeutic regimens that involve a short-term BAFF antagonist administration course followed by an extended no-treatment period prior to the next round of administration.

In one aspect, the invention provides a therapeutic regimen for treating a patient having an immunologic or a related disorder. The regimen comprises:

(a) administering to the patient a therapeutically effective amount of a BAFF (B cell activating factor belonging to the TNF family) antagonist at least once or at one or more intervals of less than N weeks;

(b) temporarily discontinuing the administration of step (a) for N weeks or longer; and (c) repeating steps (a) and (b) at least once;

wherein N is 8, 9, 10, 11, or 12.

In further embodiments, the administration of step (a) comprises an interval of 1, 2, 3, 4, 5, 6, or 7 weeks. In step (a), the BAFF antagonist may, for example, be administered 2, 3, 4, 5, 6, or 7 times a week, weekly, biweekly, every 3, 4, 5, 6, 7, 8, 9, 10, 11, or 12 weeks. In the administration period of step (a), the intervals between sequential administrations as well as dosages may vary. For example, in the administration period of step (a), the BAFF antagonist may be administered twice in the first week, withdrawn for three weeks, administered once, withdrawn for next 5 weeks, then administered daily for a week. In various embodiments, the administration is temporarily discontinued, as in step (b), for 8, 9, 10, 11, 12, 18, 24, 30, 36, 42, 48 weeks or a longer period which may be limited to 50, 80, 110, 140, 180, 210, 260, or 300 weeks.

In one aspect, the invention provides methods for treating immunologic and related disorders in mammals, in particular autoimmune disorders, and includes (but is not limited to) methods for reducing autoantibody titer (e.g., anti-nuclear antibodies such as, for example, anti-ssDNA, anti-Sm, anti-RNP, and anti-Ro).

In another aspect, the invention further provides methods for treating renal fibrosis and/or improving renal function, such as, e.g., pressure filtration, selective reabsorption, tubular secretion, and systemic blood pressure regulation. In yet another aspect, the invention yet further provides methods for decreasing cardiac inflammation.

The invention further provides a method of reducing a pathogenic B cell population in a patient having an immune disorder. In certain embodiments, the pathogenic population of B cells is composed of B cells that are IgM-IgD+. B cell populations can be determined using, for example, antibodies to commonly used B cell markers such as, e.g., the B220 isoform of CD45 (Kincade et al. (1981) J. Immunol., 127: 2262-2268), or CD19 (see e.g., Krop et al. (1996) Eur. J. Immunol., 26:238-242) and respective isotype anti-immunoglobulin antibodies using methods known in the art and/or as described in the Examples.

The compositions of the invention may be administered in any manner that is medically acceptable. "Administration" is not limited to any particular delivery system and may include, without limitation, parenteral (including subcutaneous, intravenous, intramedullary, intraarticular, intramuscular, or intraperitoneal injection) rectal, topical, transdermal, or oral (for example, in capsules, suspensions, or tablets). Administration to an individual may occur in a single dose or in repeat administrations, and in any of a variety of physiologically acceptable salt forms, and/or with an acceptable pharmaceutical carrier and/or additive as part of a pharmaceutical composition (described earlier). Physiologically acceptable salt forms and standard pharmaceutical formulation techniques and excipients are well known to persons skilled in the art (see, e.g., Physicians' Desk Reference (PDR) 2003, 57th ed., Medical Economics Company, 2002; and Remington: The Science and Practice of Pharmacy, eds. Gennado et al., 20th ed, Lippincott, Williams & Wilkins, 2000).

Administration of an antagonist to an individual may also be accomplished by means of gene therapy, wherein a nucleic acid sequence encoding the antagonist is administered to the patient in vivo or to cells in vitro, which are then introduced into a patient, and the antagonist (e.g., antisense RNA, soluble BAFF receptor) is produced by expression of the product encoded by the nucleic acid sequence.

In certain embodiments, the patient to be treated using the methods of the invention has mild, moderate, or severe disease. In various embodiments, patients are those having an immunologic disorder and/or are at increased risk for developing renal insufficiency. The treatment may be particularly useful in patients with proteinuria of over 1, 1.2, 1.5, 1.7, 2.0 g per a 24-hour period, and/or serum creatinine levels of 1.0, 1.5, 2.0, 2.5 mg/dl or higher. Other indications include creatinine clearance levels of lower than 97, 90, 80, 70, 60 (men) and 88, 80, 70, 60 (women) ml/min, blood urea of 20, 25, 30 mg/dl or higher, and/or those indicated by renal imaging (e.g., MRI, ultrasound), or renal biopsy. Yet other indications include above normal titer of antinuclear antibodies in the serum (e.g., anti-ssDNA, anti-Sm, anti-RNP, and anti-Ro) or above normal peripheral blood B cell (e.g., CD19+) counts of over 700, 1000, 1250, 1500, 2000 cells/μl. Tests for assessing these parameters can be preformed using methods known in the art, as described in the Examples, or in Jacobs et al. (eds.) (2002) Laboratory test handbook: Concise with disease index (2nd ed.) Husson, Ohio, Lexi-Comp.

The methods of the invention may be also used for treating patient having immunologic disorders where there is abnormal proliferation, maturation, survival, differentiation, or function of immune cells, such as, for example, B or T cells. The methods of the invention can be useful for treating pre-B or B cell leukemias, such as plasma cell leukemia, chronic or acute lymphocytic leukemia, myelomas (e.g., multiple myeloma, plasma cell myeloma, endothelial myeloma, and giant cell myeloma), and lymphoma (e.g., non-Hodgkin's lymphoma), Burkitt's lymphoma, non-Burkitt's lymphoma, follicular lymphoma, acute lymphoblastic leukemia, large cell lymphoma (e.g., immunoblastic lymphoma), marginal zone lymphoma, mantle cell lymphoma, small lymphocytic lymphoma, other B cell lymphomas, glomerulonephritis associated with diseases such as membranous nephropathy, IgA nephropathy (Berger's disease), IgM nephropathy, Goodpasture's disease, post-infectious glomerulonephritis, mesangioproliferative disease, chronic lymphoid leukemia, and minimal-change nephritic syndrome, secondary glomerulonephritis, vasculitis, pyelonephritis, nephrocalcinosis, nephrolithiasis, chronic or acute interstitial nephritis, hypertensive or large vessel diseases (including renal artery stenosis or occlusion and cholesterol emboli or renal emboli), renal or urological neoplasms, multiple myelomas, lymphomas, light chain neuropathy, amyloidosis, asthma and other chronic airway diseases such as bronchitis and emphysema, insulin dependent diabetes mellitus, and Crohn's disease. The methods of the invention can also be used for inhibiting or neutralizing an effector T cell response and for treating conditions requiring immunosuppression, such as graft versus host disease and graft rejection, chronic inflammatory diseases, in particular, to lessen joint pain, swelling, anemia, and septic shock.

In the methods of the invention, the antagonist(s) is(are) administered as the sole active compound(s) or in combination with other compound(s) or composition(s). Unless otherwise indicated, the dose of antagonists administered is approximately 1 µg/kg and 250 mg/kg, depending on the severity of the symptoms and the progression of the disease. Most commonly, antibodies or immunoglobulin fusion proteins are administered in an outpatient setting by weekly administration of about 0.1-10 mg/kg doses by slow intravenous (IV) infusion. The appropriate therapeutically effective dose of an antagonist is selected by a treating clinician and would range approximately from 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 10 µg/kg to 1 mg/kg, 10 µg/kg to 100 mg/kg, 100 µg to 1 mg/kg, or 500 µg/kg to 5 mg/kg. Alternatively, specific dosages indicated in the Examples or for similar drugs in the Physicians' Desk Reference (PDR) 2003, 57th ed., Medical Economics Company, 2002, may be used.

Compositions

BAFF antagonists used in the methods of the present invention, include (but are not limited to) antibodies directed against BAFF, antibodies directed against one or more isoforms of at least one BAFF receptor, and soluble forms of BAFF receptors.

BAFF receptors include BAFFR (SEQ ID NO:1) BCMA (SEQ ID NO:7), and TACI (SEQ ID NO 8). In some embodiments, the BAFF antagonist is BAFF-specific (e.g., BAFFR), while in certain other embodiments the BAFF antagonist may also bind TNF family ligands other than BAFF (e.g., BCMA and TACI which also bind to APRIL), In some embodiments, the BAFF antagonist is an antibody that blocks BAFF binding to its receptor. Antibodies directed to BAFF and to BAFF receptors have been previously described. Producing such antibodies is well known in the art (see. e.g., Antibody Engineering, ed. Borrebaeck, 2nd ed., Oxford University Press, 1995). Examples of antibodies for use in the methods of the invention include those described in PCT Publication WO 99/12964 and U.S. patent application Ser. No. 09/911,777 and the anti-BAFF antibody LymphoStat-B™ (Human Genome Sciences, Rockville, Md.). In further embodiments, the antibody of the invention may specifically bind, besides BAFF or BAFFR, another protein that is substantially identical to BAFF or BAFFR, respectively. In yet further embodiments, antibodies are directed against BCMA and/or TACI. Also contemplated for use in humans are humanized forms and derivatives of nonhuman antibodies derived from any vertebrate species.

Other examples of antibodies for use in the methods of the invention include mouse monoclonal antibodies produced by hybridoma clone #2.1, deposited as ATCC No. PTA-3689, or by clone #9.1, deposited as ATCC No. PTA-3688, or humanized chimeric, or fully human derivatives thereof.

Soluble forms of BAFF receptor fusion proteins may comprise a BAFF-binding domain of BAFFR, BCMA, and/or TACI. A BAFF-binding domain is located within the extracellular domains (ECD), i.e., the portion of the protein normally present on the exterior of a cell expressing the protein. In some embodiments, the soluble BAFFR is a disulfide-linked peptide having the sequence CHWDLLRHWVC (SEQ ID NO:5) (Kayagaki et al. (2002) Immunity, 10:515-524), or a polypeptide comprising this sequence. In yet other embodiments, the soluble BAFFR is a polypeptide comprising amino acids 27 to 32 or 18 to 43 of SEQ ID NO:1.

In certain embodiments, a soluble form a BAFF receptor comprises a BAFF-binding domain of a BAFF receptor fused to a constant region of an immunoglobulin, i.e., as in BAFFR-Fc. In same embodiments, BAFFR-Ig comprises residues 3 to 73 of SEQ ID NO:1 used to the Fc portion of IgG. In illustrative embodiments, BAFFR-Fc comprises SEQ ID NO:2 (human) or SEQ ID NO:4 (murine). In some embodiments, BAFFR is a human BAFFR having a C-terminal deletion starting from amino acid 51 of SEQ ID NO:1, which results in an altered O-linked glycosylation pattern (e.g., ΔBAFFR described in U.S. Patent Application No. 60/458,707). In some embodiments, soluble BAFFR comprises ΔBAFFR which lacks at least the sequence of SEQ ID NO:6 (corresponding to amino acids 51-57 of SEQ ID NO:1).

The BASE-binding domain of BAFFR comprises amino acids (as) 8 to aa 50, as 13 to aa 50, or as 13 to aa 43, or aa 18 to aa 43 of SEQ ID NO:1. In certain embodiments, the BAFF-binding domain is identical or substantially identical to aa 2 to aa 63 of SEQ ID NO:1 or to aa 2 to aa 62 of SEQ ID NO:3, including sequences that have been truncated or mutated so long as such sequences retain the ability to bind BASE. In illustrative embodiments, BAFFR is a murine sequence as set out from as 2 to aa 66 of SEQ ID NO:3. In other embodiments, BAFFR comprises at least 20, 25, 30, 35, 40, 45, or 50 contiguous amino acids of SEQ ID NO:1.

In certain embodiments, the constant region of an immunoglobulin comprises any one of CH1, CH2, or CH3 constant regions, or the entire Fc portion (that includes CH2, or CH3), with or without a hinge region. In more embodiments, the second amino acid sequence is derived from the Fc portion of an IgG. In related embodiments, the Fc portion is derived from IgG1, IgG4, or another IgG isotype. In illustrative embodiments, the contract region of an immunoglobulin comprises a sequence from aa 95 to aa 321 of SEQ ID NO:3, or aa 88 to aa 316 of SEQ ID NO:4. The second amino acid sequence may comprise the Fc portion of human IgG1 wherein the Fc is modified to minimize the effector function. Such modifications include changing specific amino acid residues that might alter an effector function such as Fc receptor binding (Lund et al. (1991) J. Immuno., 147:2657-2662 and Morgan et al. (1995) Immunology, 86:319-324), or changing the species from which the constant region is derived. Immunoglobulins may have mutations in the CH2 region of the heavy chain that reduce effector function, i.e., Fc receptor binding and complement activation. For example, immunoglobulins may have mutations such as those described in U.S. Pat. Nos. 5,624,821 and 5,648,260. In the IgG1 or IgG2 heavy chain, for example, such mutations may be made at amino acid residues corresponding to amino acids 234 and 237 in the full-length sequence of IgG1 or IgG2. Antibodies and immunoglobulin-receptor fusion proteins may also have mutations that stabilize the disulfide bond between the two heavy chains of an immunoglobulin, such as mutations in the hinge region of IgG4, as disclosed in Angal et al. (1993) Mol. Immunol., 30:105-108.

In certain embodiments, a BAFF-binding domain is fused at the C-terminus or the N-terminus, with or without a linker sequence, to the C-terminus or the N-terminus of the constant region of an immunoglobulin. The exact length and sequence of the linker and its orientation relative to the linked sequences may vary. The linker may, for example, comprise one or more Gly-Ser. The linker may be 2, 10, 20, 30, or more amino acid long and is selected based on properties desired such as solubility, length and steric separation, immogenicity, etc. It will be understood by one of ordinary skill in the art that certain amino acids in a sequence of any protein may be substituted for other amino acids without adversely affecting the activity of the protein. It is thus contemplated that various changes may be made in the amino acid sequences of BAFF receptor of the invention, or DNA sequences encoding therefore, as provided, without appreciable loss of their biological activity or utility.

The use of derivatives and analogs of BAFF receptors are also within the scope of the present invention. The derivatives or analogs should be functionally active, i.e., capable of exhibiting one or more activities associated with a ligand-binding domain of the wild-type BAFFR. Derivatives or analogs that retain this binding ability, or inhibit biological activity of BAFF can be produced and tested by procedures known in the art and/or as described in the Examples. Methods of producing such derivatives and analogs include recombinant and synthetic methods (see, e.g., Maniatis (1990) Molecular Cloning; A Laboratory Manual, 2nd ed., Cold Spring Harbor Laboratory, Cold Spring Harbor, N.Y., and Bodansky et al. (1995) The Practice of Peptide Synthesis, 2nd ed., Spring Verlag, Berlin, Germany).

The following examples provide illustrative embodiments of the invention. While the representative procedures are performed in mice, a skilled artisan recognizes that they can be successfully performed within parameters clinically feasible in human subjects. The skilled artisan will recognize the numerous modifications and variations that may be performed without altering the spirit or scope of the present invention. Such modifications and variations are encompassed within the scope of the invention. The examples do not in any way limit the invention.

Examples

The following describes materials and methods used in the representative procedures and experiments described in the subsequent Examples.

Mice

Female (SWR×NZB)F1 (SNF1) mice were bred and maintained as previously described in, e.g., Gavalchin et al. (1987) J. Immunol., 138:138-148; Datta et al. 1989 Clin. Immunol. Immunopathol., 51:141-56.

Protein Reagents

An expression vector containing murine BAFFR-muIgG1 (BAFFR-Fc) was constructed by ligating a Not1+Aat2 fragment containing a signal sequence from a murine Ig-k gene, an Aat2+Sal1 fragment containing the sequence encoding aa 2 to aa 66 of murine BAFFR (Accession No. AF373847) and a Sal+Not1 fragment containing the sequence encoding as 226 to aa 478 of murine IgG1 (Kabat system of numbering) into the Not1 site of a modified version (without the EBNA-1 gene) of pCEP4 (Invitrogen, Carlsbad, Calif.), called CH269. The vector was transfected into 293 cells containing the EBNA-1 gene using Lipofectamine™ according to the manufacturer's protocol (Invitrogen). The transfection was maintained in Dulbecco's modified Eagle's medium (DMEM) supplemented with 10% fetal calf serum (FCS), 2 mM glutamine, 100 U/ml penicillin, 100 µg/ml streptomycin and 250 µg/ml G418. Medium was harvested every 4-7 days for several weeks. The conditioned medium was diluted with three volumes of high salt and high pH buffer (1.5 M glycine pH 8.9, 3 M NaCl) to increase the affinity of mBAFFR-mIgG for protein A. The BAFFR-Fc protein was purified by affinity chromatography (protein A) followed by size exclusion chromatography. Mouse IgG1 (mIgG1), produced by the MOPC21 hybridoma was purified in a similar fashion and was used as a negative control.

Treatment Protocol

Twenty 23 week-old female SNF1 mice with established nephritis (proteinuria of 30-100 mg/dl) were divided into two cohorts of ten mice/group. One cohort received 200 µg of mouse BAFFR-Fc and the other received 200 µg of mIgG1, 2 times per week for 4 consecutive weeks, and monitored thereafter for progression of disease. Mice that became moribund were euthanized, and tissues and blood samples were collected for analysis prior to sacrifice. Blood was also collected via the retro-orbital sinus at regular intervals for obtaining serum for autoantibody determination. At termination of the study, kidneys, hearts, and mesenteric lymph nodes (MLN) were placed in 19% neutral buffered saline and embedded into paraffin blocks for histologic analysis. The spleens were collected and used for flow cytometry.

Flow Cytometry

Single cell suspensions were made of splenocytes by mechanical disruption. Erythrocytes were lysed in an ammonium chloride solution, and cells were then washed 3 times, filtered through a 100-micron filter, and counted using a hemocytometer. Splenocytes were stained with a fluorochrome-conjugated anti-B220 mAb to detect B lymphocytes as described in Thompson et al. (2001) Science, 293:2108-2111.

Histology

Paraffin-embedded mesenteric lymph nodes (MLN) and kidney sections were assessed lymphocyte infiltration using rat anti-B220 mAb for B cells and rat anti-CD3 mAb for T cells, followed by biotinylated rabbit anti-rat and avidin-biotin-HRP solution, and visualized using the substrate DAB (Vector Laboratories, Burlingame, Calif.). Kidney fibrosis was assessed by staining kidneys with Mason's trichrome stain and biotin-labeled anti-α smooth muscle actin followed by incubation with streptavidin-HAP and visualized with DAB substrate. Slides were counterstained with Mayer's hematoxylin. Heart inflammation was assessed by examination of H&E-stained heart tissues.

Assessment of Renal and Cardiac Disease

The urine of each mouse was monitored weekly with Albustix™ (Bayer Corp., Research Triangle Park, N.C.) to measure proteinuria. H&E-stained kidney sections were used for histologic examination and scored for: glomerular hypercellularity, enlargement, crescents, mesangial thickening, loops, fibrinoid necrosis and hyaline; interstitial sclerosis, infiltrate and vasculitis; and tubule vasculitis, atrophy and casts. Heart tissues were examined for vascular and cardiac inflammation and cardiac vacuolation. The grades of 0-4+ were given based on percent involvement of the structure being examined, wherein 0=none and 4+ is 100% involvement.

ELISA

The ELISA assay used to detect serum anti-ssDNA antibody was performed as described in Kalled et al. (1998) J. Immunol., 160:2158-2165.

Example 1

Short-Term BAFFR-Fc Administration Increases Survival

As shown in Table 1, a short-course of BAFFR-Fc treatment markedly enhanced survival when compared to mIgG control-treated mice. At age 49 weeks, all BAFFR-Fc-treated mice were alive, while only 30% of control mice remained alive.

TABLE 1

| Age | Percent survival Treatment | |
|---|---|---|
| (weeks) | BAFFR-Fc | mIgG |
| 23 | 100 | 100 |
| 29 | 100 | 100 |
| 30 | 100 | 90 |
| 31 | 100 | 90 |
| 32 | 100 | 80 |
| 33 | 100 | 70 |
| 34 | 100 | 30 |
| 49 | 100 | 30 |

Example 2

Short-Term BAFFR-Fc Administration Reduces Progression of Nephritis

Renal function was assessed by proteinuria determination at regular intervals. As shown in Table 2, progression of disease to severe nephritis (proteinuria ≥300 mg/dL) was significantly reduced in BAFFR-Fc-treated mice when compared to mIgG-treated control Mice. By age 49 weeks, all control mice developed severe nephritis, while no BAFFR-Fc-treated animal had severe nephritis at that age. In a separate experiment, SNF1 mice were treated with human IgG or with human TACI-Fc (a receptor-Fc fusion protein that binds to both BAFF and APRIL) at 200 μg twice per week for four weeks. Although TACI-Fc administration somewhat reduced the incidence of severe nephritis initially, eventually all TACI-Fc-treated mice developed severe nephritis similarly to controls (Table 2).

TABLE 2

| | Percent incidence of severe nephritis Treatment | | | |
|---|---|---|---|---|
| Age (wks) | BAFFR-Fc | mIgG | Human TACI-Fc | Human IgG |
| 23 | 0 | 0 | 0 | 0 |
| 27 | 0 | 30 | 34 | 60 |
| 30 | 0 | 70 | 60 | 80 |
| 36 | 0 | 90 | 100 | 100 |
| 49 | 0 | 100 | 100 | 100 |

Renal disease was further assessed by an histologic approach. H&E stained kidney sections were scored for renal disease by combining the scores of the individual disease parameters described in Materials and Methods. As seen in Table 3, BAFFR-Fc-treated mice had significantly reduced cumulative disease scores when compared to mIgG-treated or untreated controls, and the scores of BAFFR-Fc-treated mice were closer to that of young SNF1 mice, prior to disease onset.

TABLE 3

| | Cumulative kidney disease score (mean ± SD) | | |
|---|---|---|---|
| Age (weeks) | BAFFR-Fc | untreated | mIgG |
| 9 | | 1 ± 0 (n = 3)[1] | |
| 49-51 | 6.3 ± 2.5 (n = 10) | 24.3 ± 8.6 (n = 4) | 23.9 ± 8.6 (n = 7) |

[1]n indicates the number of mice used in analysis.

In SLE-nephritis, renal fibrosis often occurs and may be mediated by secretion of extracellular matrix (ECM) proteins, α-smooth muscle actin (ASMA) and collagen, by fibroblasts and mesangial cells. ECM production was significantly ($p<0.05$, Student's t test) diminished in mice treated with BAFFR-Fc as compared to untreated and mIgG-treated SNF1 mice, as observed by reduced ASMA (Table 4) and Collagen (Table 5) deposition in the kidneys. Young, 9 week-old SNF1 mice were used as pre-disease controls.

TABLE 4

| | Percent glomeruli exhibiting collagen deposition[1] (mean ± SD) | | |
|---|---|---|---|
| Age (weeks) | BAFFR-Fc | untreated | mIgG |
| 9 | | 0 (n = 3) | |
| 49-51 | 3.3 ± 8.8 (n = 10) | 48.2 ± 36.2 (n = 4) | 68.8 ± 33.2 (n = 7) |

[1]70-111 glomeruli were examined for each mouse.

TABLE 5

| | Percent glomeruli exhibiting ASMA production[1] (mean ± SD) | | |
|---|---|---|---|
| Age (weeks) | BAFFR-Fc | untreated | mIgG |
| 9 | | 0 (n = 3) | |
| 49-51 | 8.5 ± 10.9 (n = 10) | 57.5 ± 29.5 (n = 4) | 68.5 ± 32.1 (n = 7) |

[1]70-111 glomeruli were examined for each mouse.

Healthy kidneys do not harbor lymphoid clusters. However, accompanying disease in this model of SLE-nephritis, as well as in human disease, is infiltration of leukocytes into the kidney, including B and T cells, forming follicular-like structures. Therefore, kidney sections were examined for the presence of T and B cell infiltrates. In untreated (FIG. 1B) and mIgG-treated (FIG. 1D) mice, large areas of T and B cell infiltrates that mimic white pulp areas of secondary lymphoid tissues were observed throughout the kidneys. In contrast, in kidneys of mice that received short-term BAFFR-Fc treatment (FIG. 1C), infiltration of B cells, as well as T cells, was markedly reduced (FIG. 1). Few or no B or T cells were observed in healthy, 9 week-old (pre-disease) SNF1 Mice (FIG. 1A).

Example 3

Short-Term BAFFR-Fc Administration Inhibits Cardiac Inflammation

H&E-stained paraffin sections of hearts were examined for vascular and cardiac inflammation, and cardiac vacuolation. As seen in Table 6, SNF1 mice that received BAFFR-Fc had an overall markedly reduced cardiac score when compared to mIgG and untreated control mice.

TABLE 6

| | Cardiac score (mean ± SD) | | |
|---|---|---|---|
| Age (weeks) | BAFFR-Fc | untreated | mIgG |
| 9 | | 0 (n = 3)[1] | |
| 49-51 | 1.2 ± 0.4 (n = 10) | 2.5 ± 1.1 (n = 4) | 4.7 ± 1.9 (n = 3) |

[1]n indicates the number of mice used in the analysis.

Example 4

Short-Term BAFFR-Fc Administration Prevents B Cell Hyperplasia

Based on a study of BAFF blockade in normal BALB/c mice with BAFFR-Fc, 100 μg once a week for 4 consecutive weeks, peripheral B cell numbers are known to be fully restored within about 9 weeks after the last dose of BAFFR-Fc (data not shown). The number of splenic B cells in the SNF1 mice was determined 26-28 weeks after the last dose of BAFFR-Fc or mIgG. As seen in Table 7, SNF1 mice that received a short course of BAFFR-Fc treatment had a significantly reduced (p<0.05, Student's t test) splenic B cell number than untreated or mIgG-treated control mice. With time, control mice developed severe splenic B cell hyperplasia. In contrast, BAFFR-Fc-treated mice exhibited a long-term benefit wherein at the end of the study, splenic B cell counts were between that of pre-disease, 9 Week-old SNF1 mice, and 20 Week-old SNF1 mice that have begun to experience B cell expansion.

TABLE 7

| | Number of splenic B cells (×10$^6$) | | |
|---|---|---|---|
| Age (weeks) | BAFFR-Fc | untreated | mIgG |
| 9 | | 34.3 ± 9 (n = 3) | |
| 20 | | 123 (n = 1) | |
| 49-51 | 77.4 ± 41.7 (n = 10) | 197.4 ± 62 (n = 4) | 141 ± 70.6 (n = 3) |

Figure 2A:
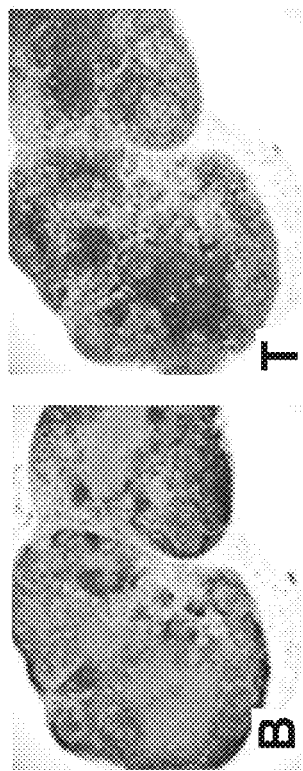
FIGS. 2A-2D demonstrate that a short-term BAFFR-Fc treatment inhibits lymphadenopathy in SNF1 mice as assessed by immunohistochemistry on paraffin-embedded mesenteric lymph node (MLN) sections using biotin-anti-B220 mAb for B cells and anti-CD3 for T cells (50× magnification).
Figure 2B:
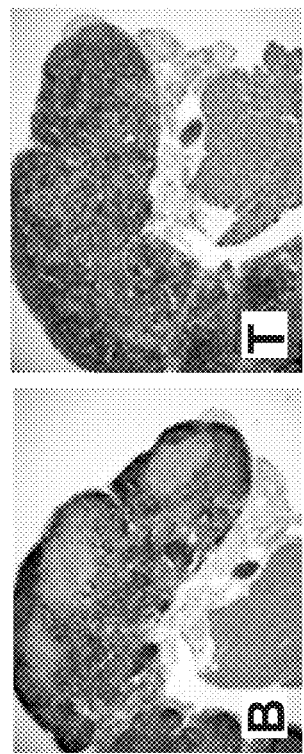
Figure 2C:
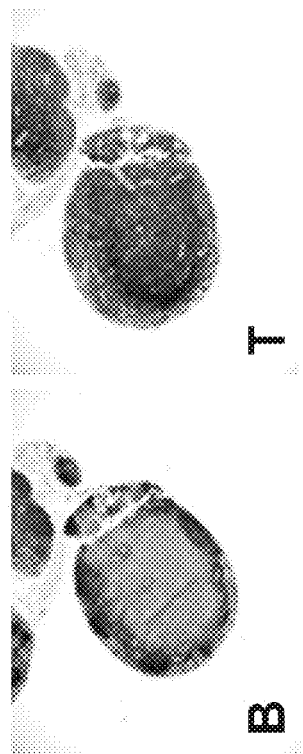
Figure 2D:
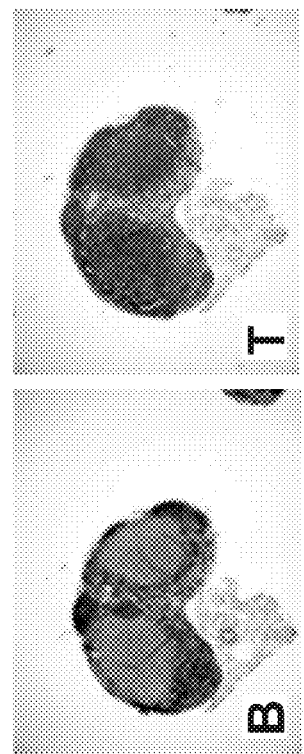

In addition, immunohistochemical analysis of the B and T cell organization in MLN demonstrated that untreated (FIG. 2B) and mIgG-treated (FIG. 2D) mice had extensive B cell expansion, resulting in lymphadnopathy. In contrast, BAFFR-Fc-treated mice (FIG. 2C), did not exhibit B cell hyperplasia and looked similar to young SNF1 mice prior to disease onset (FIG. 2A).

Example 5

Short-Term BAFFR-Fc Administration Inhibits Increasing Production of Autoantibody Sera obtained from SNF1 mice at regular intervals were analyzed for circulating anti-ssDNA antibody using an ELISA format. When examining the change of anti-ssDNA levels with time, from the start of treatment to age 37 weeks, there is a significant change (increase) in anti-ssDNA in the mIgG-treated mice (p<0.05 using the Student-Newman-Keuls method), however, there is no significant change in autoantibody levels in mice that received BAFFR-Fc (Table 8). This indicates that BAFF blockade with BAFFR-Fc inhibits autoantibody production, which may contribute to decreased pathology in BAFFR-Fc-treated mice. Notably, autoantibody levels remained decreased compared with controls 10 weeks (age 37 weeks) after the last dose of BAFFR-Fc had been administered.

TABLE 8

| | Anti-ssDNA (μg/ml) Treatment | |
|---|---|---|
| Age (weeks) | BAFFR-Fc (n = 10) | mIgG (n = 10) |
| 23 | 0.1[1] | 0.15 |
| 29 | 0.4 | 1.1 |
| 37 | 0.7 | 24.3 |

[1]Values reflect geometric means.

Example 6

Short-Term BAFFR-Fc Administration Reduces Percentage of IgM$^-$IgD$^+$ B Cells

At the end of the study, BAFFR-Fc-treated and mIgG-treated mice had a similar frequency of total B cells in the blood, based on staining for B220$^+$ B cells. However, when specific B cell subsets were examined, BAFFR-Fc-treated mice exhibited a statistically significant reduction (p<0.01, Student's t test) in the percent of IgM$^-$IgD$^+$ B cells (Table 9). The general reconstitution of peripheral B cells, yet the selective, marked-reduction in IgM$^-$IgD$^+$ B cells and long-team efficacy in BAFFR-Fc-treated mice suggests that BAFFR-Fc causes a long-term reduction in, these presumably pathogenic B cells.

TABLE 9

| | Percent blood B cells (mean ± SD) | |
|---|---|---|
| | BAFFR-Fc[1] | mIgG[1] |
| IgM$^-$IgD$^+$ B cells | 8.7 ± 5.0 | 44.9 ± 7.3 |
| Total B220$^+$ B cells | 47.3 ± 9.3 | 49.6 ± 8.6 |

[1]Mice were 49-51 weeks of age at the time of analysis.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents and sequences cited in this disclosure are incorporated by reference in their entirety. To the extent the material incorporated by reference contradicts or is inconsistent with the present specification, the present specification will supersede any such material. The citation of any references herein is not an admission that such references are prior art to the present invention.

The following applies unless otherwise indicated: ail numbers expressing quantities of ingredients, cell culture, treatment conditions, and so forth used in the specification, including claims, are to be understood as being modified in all instances by the term "about"; the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

The invention claimed is:

1. A method of treating a patient having an autoimmune disorder, comprising:
   (a) administering to the patient a therapeutically effective amount of a soluble BCMA (B cell maturation antigen) polypeptide at least once or at one or more intervals of less than N weeks;
   (b) temporarily discontinuing the administration of step (a) for N weeks or longer; and
   (c) repeating steps (a) and (b) at least once;
   wherein N is 8, 9, 10, 11, or 12.

2. The method of claim 1, wherein the administration of step (a) comprises an interval of 1, 2, 3, 4, 5, 6, or 7 weeks.

3. The method of claim 1, wherein the soluble BCMA polypeptide is administered in step (a) 2, 3, 4, 5, 6, or 7 times a week.

4. The method of claim 1, wherein the administration is discontinued in step (b) for 12, 18, 24, 30, 36, 42, 48 weeks or longer.

5. The method of claim 1, wherein at the beginning of the treatment the patient has one or more of:
   (i) proteinuria of 1 g per a 24-hour period or higher;
   (ii) serum creatinine levels of about 1 mg/dl or higher;
   (iii) creatinine clearance levels of 97 ml/min or lower;
   (iv) blood urea of 20 mg/dl or higher;
   (v) abnormal titer of autoantibodies in the serum; and
   (vi) peripheral blood B cell count of 700 cells/µl.

6. The method of claim 5, wherein the patient is human.

7. The method of claim 1, wherein the therapeutically effective amount of the soluble BCMA polypeptide is sufficient to inhibit autoantibody titer.

8. The method of claim 1, wherein the therapeutically effective amount of the soluble BCMA polypeptide is sufficient to reduce B cell hyperplasia.

9. The method of claim 1, wherein the therapeutically effective amount of the soluble BCMA polypeptide is sufficient to reduce cardiac inflammation.

10. The method of claim 1, wherein the therapeutically effective amount of the soluble BCMA polypeptide is sufficient to improve renal function.

11. The method of claim 10, wherein the renal function is one or more of: pressure filtration, selective reabsorption, tubular secretion, and systemic blood pressure regulation.

12. The method of claim 1, wherein the therapeutically effective amount of the soluble BCMA polypeptide is sufficient to reduce progression of renal fibrosis.

13. The method of claim 1, wherein the therapeutically effective amount of the soluble BCMA polypeptide is sufficient to reduce lymphocyte infiltration in the kidneys.

14. The method of claim 1, wherein the therapeutically effective amount of the soluble BCMA polypeptide is sufficient to reduce lymphadenopathy.

15. The method of claim 1, wherein the autoimmune disorder is systemic lupus erythematosus.

16. The method of claim 1, wherein the soluble BCMA polypeptide is fused to a constant region of an immunoglobulin.

17. The method of claim 16, wherein the immunoglobulin is $IgG_1$ or $IgG_4$.

18. The method of claim 16, wherein the constant region of an immunoglobulin comprises an Fc portion.

19. A method of reducing autoantibody titer in a patient in need thereof, comprising:
   (a) administering to the patient a therapeutically effective amount of a soluble BCMA (B cell maturation antigen) polypeptide at least once or at one or more intervals of less than N weeks;
   (b) temporarily discontinuing the administration of step (a) for N weeks or longer; and
   (c) repeating steps (a) and (b) at least once;
   thereby reducing autoantibody titer, and wherein N is 8, 9, 10, 11, or 12.

20. A method of inhibiting generation of pathogenic B cells in a patient in need thereof, comprising:
   (a) administering to the patient a therapeutically effective amount of a soluble BCMA (B cell maturation antigen) polypeptide at least once or at one or more intervals of less than N weeks;
   (b) temporarily discontinuing the administration of step (a) for N weeks or longer; and
   (c) repeating steps (a) and (b) at least once;
   thereby inhibiting generation of pathogenic B cells, and wherein N is 8, 9, 10, 11, or 12.

21. The method of claim 20, wherein the pathogenic B cells are $IgM^-IgD^+$.

* * * * *

SEQUENCE LISTING

<160> NUMBER OF SEQ ID NOS: 8

<210> SEQ ID NO 1
<211> LENGTH: 186
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: None, or any amino acid
<220> FEATURE:
<221> NAME/KEY: MISC_FEATURE
<222> LOCATION: (2)..(2)
<223> OTHER INFORMATION: Methionine, none, or any amino acid
<220> FEATURE:
<221> NAME/KEY: MISC_FEATURE
<222> LOCATION: (21)..(21)
<223> OTHER INFORMATION: valine (wild type), asparagine, or another
      amino acid
<220> FEATURE:
<221> NAME/KEY: MISC_FEATURE
<222> LOCATION: (28)..(28)
<223> OTHER INFORMATION: lysine (wild type), proline, or another amino
      acid
<220> FEATURE:
<221> NAME/KEY: MISC_FEATURE
<222> LOCATION: (47)..(47)
<223> OTHER INFORMATION: None, any amino acid, or alanine

<400> SEQUENCE: 1

Xaa Xaa Arg Arg Gly Pro Arg Ser Leu Arg Gly Arg Asp Ala Pro Ala
 1               5                  10                  15

Pro Thr Pro Cys Xaa Pro Ala Glu Cys Phe Asp Xaa Leu Val Arg His
                20                  25                  30

Cys Val Ala Cys Gly Leu Leu Arg Thr Pro Arg Pro Lys Pro Xaa Ala
            35                  40                  45

Gly Ala Ser Ser Pro Ala Pro Arg Thr Ala Leu Gln Pro Gln Glu Ser
        50                  55                  60

Val Gly Ala Gly Ala Gly Glu Ala Ala Leu Pro Leu Pro Gly Leu Leu
65                  70                  75                  80

Phe Gly Ala Pro Ala Leu Leu Gly Leu Ala Leu Val Leu Ala Leu Val
                85                  90                  95

Leu Val Gly Leu Val Ser Trp Arg Arg Arg Gln Arg Arg Leu Arg Gly
            100                 105                 110

Ala Ser Ser Ala Glu Ala Pro Asp Gly Asp Lys Asp Ala Pro Glu Pro
        115                 120                 125

Leu Asp Lys Val Ile Ile Leu Ser Pro Gly Ile Ser Asp Ala Thr Ala
130                 135                 140

Pro Ala Trp Pro Pro Pro Gly Glu Asp Pro Gly Thr Thr Pro Pro Gly
145                 150                 155                 160

His Ser Val Pro Val Pro Ala Thr Glu Leu Gly Ser Thr Glu Leu Val
                165                 170                 175

Thr Thr Lys Thr Ala Gly Pro Glu Gln Gln
            180                 185

<210> SEQ ID NO 2
<211> LENGTH: 321
<212> TYPE: PRT
<213> ORGANISM: Homo sapiens
<220> FEATURE:
<221> NAME/KEY: MISC_FEATURE
<222> LOCATION: (41)..(41)
<223> OTHER INFORMATION: Valine, asparagine, or another amino acid
<220> FEATURE:
<221> NAME/KEY: MISC_FEATURE

```
<222> LOCATION: (48)..(48)
<223> OTHER INFORMATION: Lysine (wild type), proline, or another amino
      acid
<220> FEATURE:
<221> NAME/KEY: MISC_FEATURE
<222> LOCATION: (67)..(67)
<223> OTHER INFORMATION: none, any amino acid, or alanine

<400> SEQUENCE: 2
```

| | | | | | | | | | | | | | | |
|---|---|---|---|---|---|---|---|---|---|---|---|---|---|---|
| Met | Glu | Thr | Asp | Thr | Leu | Leu | Leu | Trp | Val | Leu | Leu | Leu | Trp | Val | Pro |
| 1 | | | | 5 | | | | | 10 | | | | | 15 | |
| Gly | Ser | Thr | Gly | Asp | Val | Arg | Arg | Gly | Pro | Arg | Ser | Leu | Arg | Gly | Arg |
| | | | 20 | | | | | 25 | | | | | 30 | | |
| Asp | Ala | Pro | Ala | Pro | Thr | Pro | Cys | Xaa | Pro | Ala | Glu | Cys | Phe | Asp | Xaa |
| | | 35 | | | | | 40 | | | | | 45 | | | |
| Leu | Val | Arg | His | Cys | Val | Ala | Cys | Gly | Leu | Leu | Arg | Thr | Pro | Arg | Pro |
| | 50 | | | | | 55 | | | | | 60 | | | | |
| Lys | Pro | Xaa | Ala | Gly | Ala | Ser | Ser | Pro | Ala | Pro | Arg | Thr | Ala | Leu | Gln |
| 65 | | | | 70 | | | | | 75 | | | | | 80 | |
| Pro | Gln | Glu | Ser | Val | Gly | Ala | Gly | Ala | Gly | Glu | Ala | Ala | Val | Asp | Lys |
| | | | 85 | | | | | 90 | | | | | 95 | | |
| Thr | His | Thr | Ser | Pro | Pro | Ser | Pro | Ala | Pro | Glu | Leu | Leu | Gly | Gly | Pro |
| | | 100 | | | | | 105 | | | | | 110 | | | |
| Ser | Val | Phe | Leu | Phe | Pro | Pro | Lys | Pro | Lys | Asp | Thr | Leu | Met | Ile | Ser |
| | 115 | | | | | 120 | | | | | 125 | | | | |
| Arg | Thr | Pro | Glu | Val | Thr | Cys | Val | Val | Val | Asp | Val | Ser | His | Glu | Asp |
| 130 | | | | | 135 | | | | | 140 | | | | | |
| Pro | Glu | Val | Lys | Phe | Asn | Trp | Tyr | Val | Asp | Gly | Val | Glu | Val | His | Asn |
| 145 | | | | | 150 | | | | | 155 | | | | | 160 |
| Ala | Lys | Thr | Lys | Pro | Arg | Glu | Glu | Gln | Tyr | Asn | Ser | Thr | Tyr | Arg | Val |
| | | | | 165 | | | | | 170 | | | | | 175 | |
| Val | Ser | Val | Leu | Thr | Val | Leu | His | Gln | Asp | Trp | Leu | Asn | Gly | Lys | Glu |
| | | | 180 | | | | | 185 | | | | | 190 | | |
| Tyr | Lys | Cys | Lys | Val | Ser | Asn | Lys | Ala | Leu | Pro | Ala | Pro | Ile | Glu | Lys |
| | | 195 | | | | | 200 | | | | | 205 | | | |
| Thr | Ile | Ser | Lys | Ala | Lys | Gly | Gln | Pro | Arg | Glu | Pro | Gln | Val | Tyr | Thr |
| | 210 | | | | | 215 | | | | | 220 | | | | |
| Leu | Pro | Pro | Ser | Arg | Asp | Glu | Leu | Thr | Lys | Asn | Gln | Val | Ser | Leu | Thr |
| 225 | | | | | 230 | | | | | 235 | | | | | 240 |
| Cys | Leu | Val | Lys | Gly | Phe | Tyr | Pro | Ser | Asp | Ile | Ala | Val | Glu | Trp | Glu |
| | | | | 245 | | | | | 250 | | | | | 255 | |
| Ser | Asn | Gly | Gln | Pro | Glu | Asn | Asn | Tyr | Lys | Thr | Thr | Pro | Pro | Val | Leu |
| | | | 260 | | | | | 265 | | | | | 270 | | |
| Asp | Ser | Asp | Gly | Ser | Phe | Phe | Leu | Tyr | Ser | Lys | Leu | Thr | Val | Asp | Lys |
| | | 275 | | | | | 280 | | | | | 285 | | | |
| Ser | Arg | Trp | Gln | Gln | Gly | Asn | Val | Phe | Ser | Cys | Ser | Val | Met | His | Glu |
| | 290 | | | | | 295 | | | | | 300 | | | | |
| Ala | Leu | His | Asn | His | Tyr | Thr | Gln | Lys | Ser | Leu | Ser | Leu | Ser | Pro | Gly |
| 305 | | | | | 310 | | | | | 315 | | | | | 320 |
| Lys | | | | | | | | | | | | | | | |

```
<210> SEQ ID NO 3
<211> LENGTH: 175
<212> TYPE: PRT
<213> ORGANISM: Mus musculis

<400> SEQUENCE: 3
```

```
Met Gly Ala Arg Arg Leu Arg Val Arg Ser Gln Arg Ser Arg Asp Ser
1               5                   10                  15

Ser Val Pro Thr Gln Cys Asn Gln Thr Glu Cys Phe Asp Pro Leu Val
            20                  25                  30

Arg Asn Cys Val Ser Cys Glu Leu Phe His Thr Pro Asp Thr Gly His
            35                  40                  45

Thr Ser Ser Leu Glu Pro Gly Thr Ala Leu Gln Pro Gln Glu Gly Ser
        50                  55                  60

Ala Leu Arg Pro Asp Val Ala Leu Leu Val Gly Ala Pro Ala Leu Leu
65                  70                  75                  80

Gly Leu Ile Leu Ala Leu Thr Leu Val Gly Leu Val Ser Leu Val Ser
                85                  90                  95

Trp Arg Trp Arg Gln Gln Leu Arg Thr Ala Ser Pro Asp Thr Ser Glu
                100                 105                 110

Gly Val Gln Gln Glu Ser Leu Glu Asn Val Phe Val Pro Ser Ser Glu
                115                 120                 125

Thr Pro His Ala Ser Ala Pro Thr Trp Pro Pro Leu Lys Glu Asp Ala
            130                 135                 140

Asp Ser Ala Leu Pro Arg His Ser Val Pro Val Pro Ala Thr Glu Leu
145                 150                 155                 160

Gly Ser Thr Glu Leu Val Thr Thr Lys Thr Ala Gly Pro Glu Gln
                165                 170                 175

<210> SEQ ID NO 4
<211> LENGTH: 316
<212> TYPE: PRT
<213> ORGANISM: Mus musculis

<400> SEQUENCE: 4

Met Glu Thr Asp Thr Leu Leu Leu Trp Val Leu Leu Leu Trp Val Pro
1               5                   10                  15

Gly Ser Thr Gly Asp Val Gly Ala Arg Arg Leu Arg Val Arg Ser Gln
                20                  25                  30

Arg Ser Arg Asp Ser Ser Val Pro Thr Gln Cys Asn Gln Thr Glu Cys
            35                  40                  45

Phe Asp Pro Leu Val Arg Asn Cys Val Ser Cys Glu Leu Phe His Thr
        50                  55                  60

Pro Asp Thr Gly His Thr Ser Ser Leu Glu Pro Gly Thr Ala Leu Gln
65                  70                  75                  80

Pro Gln Glu Gly Ser Ala Leu Val Asp Val Pro Arg Asp Cys Gly Cys
                85                  90                  95

Lys Pro Cys Ile Cys Thr Val Pro Glu Val Ser Ser Val Phe Ile Phe
                100                 105                 110

Pro Pro Lys Pro Lys Asp Val Leu Thr Ile Thr Leu Thr Pro Lys Val
            115                 120                 125

Thr Cys Val Val Val Asp Ile Ser Lys Asp Pro Glu Val Gln Phe
            130                 135                 140

Ser Trp Phe Val Asp Asp Val Glu Val His Thr Ala Gln Thr Gln Pro
145                 150                 155                 160

Arg Glu Glu Gln Phe Asn Ser Thr Phe Arg Ser Val Ser Glu Leu Pro
                165                 170                 175

Ile Met His Gln Asp Trp Leu Asn Gly Lys Glu Phe Lys Cys Arg Val
                180                 185                 190

Asn Ser Ala Ala Phe Pro Ala Pro Ile Glu Lys Thr Ile Ser Lys Thr
```

```
                195                 200                 205
Lys Gly Arg Pro Lys Ala Pro Gln Val Tyr Thr Ile Pro Pro Lys
            210                 215                 220
Glu Gln Met Ala Lys Asp Lys Val Ser Leu Thr Cys Met Ile Thr Asp
225                 230                 235                 240
Phe Phe Pro Glu Asp Ile Thr Val Glu Trp Gln Trp Asn Gly Gln Pro
                245                 250                 255
Ala Glu Asn Tyr Lys Asn Thr Gln Pro Ile Met Asp Thr Asp Gly Ser
            260                 265                 270
Tyr Phe Val Tyr Ser Lys Leu Asn Val Gln Lys Ser Asn Trp Glu Ala
                275                 280                 285
Gly Asn Thr Phe Thr Cys Ser Val Leu His Glu Gly Leu His Asn His
            290                 295                 300
His Thr Glu Lys Ser Leu Ser His Ser Pro Gly Lys
305                 310                 315

<210> SEQ ID NO 5
<211> LENGTH: 11
<212> TYPE: PRT
<213> ORGANISM: Artificial sequence
<220> FEATURE:
<223> OTHER INFORMATION: Synthetic peptide

<400> SEQUENCE: 5

Cys His Trp Asp Leu Leu Arg His Trp Val Cys
1               5                   10

<210> SEQ ID NO 6
<211> LENGTH: 7
<212> TYPE: PRT
<213> ORGANISM: Homo sapiens

<400> SEQUENCE: 6

Ser Ser Pro Ala Pro Arg Thr
1               5

<210> SEQ ID NO 7
<211> LENGTH: 184
<212> TYPE: PRT
<213> ORGANISM: Homo sapiens

<400> SEQUENCE: 7

Met Leu Gln Met Ala Gly Gln Cys Ser Gln Asn Glu Tyr Phe Asp Ser
1               5                   10                  15
Leu Leu His Ala Cys Ile Pro Cys Gln Leu Arg Cys Ser Ser Asn Thr
            20                  25                  30
Pro Pro Leu Thr Cys Gln Arg Tyr Cys Asn Ala Ser Val Thr Asn Ser
        35                  40                  45
Val Lys Gly Thr Asn Ala Ile Leu Trp Thr Cys Leu Gly Leu Ser Leu
    50                  55                  60
Ile Ile Ser Leu Ala Val Phe Val Leu Met Phe Leu Leu Arg Lys Ile
65                  70                  75                  80
Ser Ser Glu Pro Leu Lys Asp Glu Phe Lys Asn Thr Gly Ser Gly Leu
                85                  90                  95
Leu Gly Met Ala Asn Ile Asp Leu Glu Lys Ser Arg Thr Gly Asp Glu
            100                 105                 110
Ile Ile Leu Pro Arg Gly Leu Glu Tyr Thr Val Glu Glu Cys Thr Cys
        115                 120                 125
```

```
Glu Asp Cys Ile Lys Ser Lys Pro Lys Val Asp Ser Asp His Cys Phe
130                 135                 140
Pro Leu Pro Ala Met Glu Glu Gly Ala Thr Ile Leu Val Thr Thr Lys
145                 150                 155                 160
Thr Asn Asp Tyr Cys Lys Ser Leu Pro Ala Ala Leu Ser Ala Thr Glu
                165                 170                 175
Ile Glu Lys Ser Ile Ser Ala Arg
                180

<210> SEQ ID NO 8
<211> LENGTH: 293
<212> TYPE: PRT
<213> ORGANISM: Homo sapiens

<400> SEQUENCE: 8

Met Ser Gly Leu Gly Arg Ser Arg Arg Gly Gly Arg Ser Arg Val Asp
1               5                   10                  15
Gln Glu Glu Arg Phe Pro Gln Gly Leu Trp Thr Gly Val Ala Met Arg
                20                  25                  30
Ser Cys Pro Glu Glu Gln Tyr Trp Asp Pro Leu Leu Gly Thr Cys Met
            35                  40                  45
Ser Cys Lys Thr Ile Cys Asn His Gln Ser Gln Arg Thr Cys Ala Ala
50                  55                  60
Phe Cys Arg Ser Leu Ser Cys Arg Lys Glu Gln Gly Lys Phe Tyr Asp
65                  70                  75                  80
His Leu Leu Arg Asp Cys Ile Ser Cys Ala Ser Ile Cys Gly Gln His
                85                  90                  95
Pro Lys Gln Cys Ala Tyr Phe Cys Glu Asn Lys Leu Arg Ser Pro Val
                100                 105                 110
Asn Leu Pro Pro Glu Leu Arg Arg Gln Arg Ser Gly Glu Val Glu Asn
                115                 120                 125
Asn Ser Asp Asn Ser Gly Arg Tyr Gln Gly Leu Glu His Arg Gly Ser
130                 135                 140
Glu Ala Ser Pro Ala Leu Pro Gly Leu Lys Leu Ser Ala Asp Gln Val
145                 150                 155                 160
Ala Leu Val Tyr Ser Thr Leu Gly Leu Cys Leu Cys Ala Val Leu Cys
                165                 170                 175
Cys Phe Leu Val Ala Val Ala Cys Phe Leu Lys Lys Arg Gly Asp Pro
                180                 185                 190
Cys Ser Cys Gln Pro Arg Ser Arg Pro Arg Gln Ser Pro Ala Lys Ser
                195                 200                 205
Ser Gln Asp His Ala Met Glu Ala Gly Ser Pro Val Ser Thr Ser Pro
210                 215                 220
Glu Pro Val Glu Thr Cys Ser Phe Cys Phe Pro Glu Cys Arg Ala Pro
225                 230                 235                 240
Thr Gln Glu Ser Ala Val Thr Pro Gly Thr Pro Asp Pro Thr Cys Ala
                245                 250                 255
Gly Arg Trp Gly Cys His Thr Arg Thr Thr Val Leu Gln Pro Cys Pro
                260                 265                 270
His Ile Pro Asp Ser Gly Leu Gly Ile Val Cys Val Pro Ala Gln Glu
                275                 280                 285
Gly Gly Pro Gly Ala
290
```